United States Patent [19]

Rao et al.

[11] Patent Number: 4,567,765

[45] Date of Patent: Feb. 4, 1986

[54] HIGH PRESSURE-HIGH TEMPERATURE AUTOCLAVE SYSTEM FOR TESTING FLUID SAMPLES ULTRASONICALLY

[75] Inventors: Prabhakar P. Rao; John J. Moon, Jr., both of Duncan, Okla.

[73] Assignee: Halliburton Company, Duncan, Okla.

[21] Appl. No.: 627,862

[22] Filed: Jul. 5, 1984

[51] Int. Cl.$^4$ ............................................. G01N 29/04
[52] U.S. Cl. ........................................ 73/594; 73/803
[58] Field of Search ................. 73/594, 590, 803, 597

[56] References Cited

U.S. PATENT DOCUMENTS 3,220,450  11/1965  Aronson, II et al. ............... 366/205
3,251,221  5/1966   Vogel et al. ........................... 73/594
4,259,868  4/1981   Rao et al. ............................. 73/597
4,377,087  3/1983   Rodot .................................... 73/597
4,380,930  4/1983   Podhrasky et al. .................. 73/594

Primary Examiner—Anthony V. Ciarlante
Attorney, Agent, or Firm—James R. Duzan; Thomas R. Weaver

[57] ABSTRACT

A fluid chamber assembly having an improved shape to enhance the reception of the first arrival of the signal from the transmitter transducer which has passed through the cement or fluid sample within the fluid chamber assembly and an improved sealing arrangement for the fluid chamber assembly.

10 Claims, 4 Drawing Figures

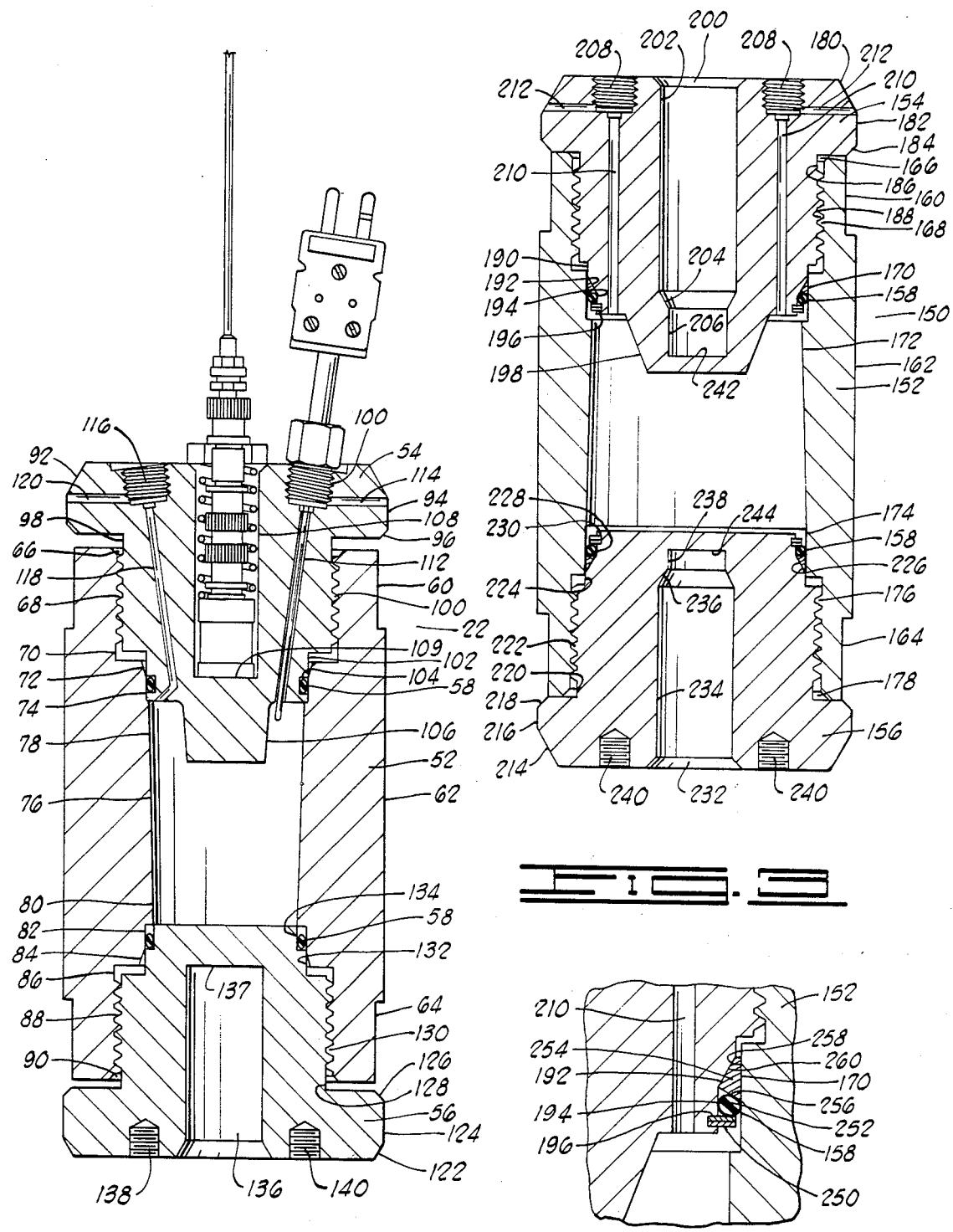

HIGH PRESSURE-HIGH TEMPERATURE AUTOCLAVE SYSTEM FOR TESTING FLUID SAMPLES ULTRASONICALLY

BACKGROUND OF THE INVENTION

This invention relates to an improved cement chamber assembly for an apparatus for the nondestructive testing of cement slurry or any fluid sample. More specifically, this invention relates to an improved fluid chamber for an apparatus for the nondestructive testing of cement as described in U.S. Pat. No. 4,259,868.

In the apparatus described in U.S. Pat. No. 4,259,868 a cement chamber assembly in a high temperature and pressure controlled autoclave houses a small cylindrical sample of the cement slurry to be tested while the autoclave maintains elevated temperature and pressure conditions as desired on the sample throughout the testing procedure.

STATEMENT OF THE INVENTION

The present invention is directed to a fluid chamber assembly having an improved shape to enhance the reception of the first arrival of the signal from the transmitter transducer which has passed through the cement or fluid sample within the fluid chamber assembly and an improved sealing arrangement for the fluid chamber assembly.

The advantages of the cement or fluid chamber assembly of the present invention will become apparent from the following description when taken in conjunction with the accompanying drawings wherein:

BRIEF DESCRIPTION OF THE DRAWINGS

FIG. 2 is a cross-sectional view of a prior art cement chamber assembly.

FIG. 3 is a cross-sectional view of the cement chamber assembly of the present invention.

FIG. 4 is a cross-sectional view of the improved seal assembly of the present invention.

DESCRIPTION OF THE INVENTION

Figure 1:
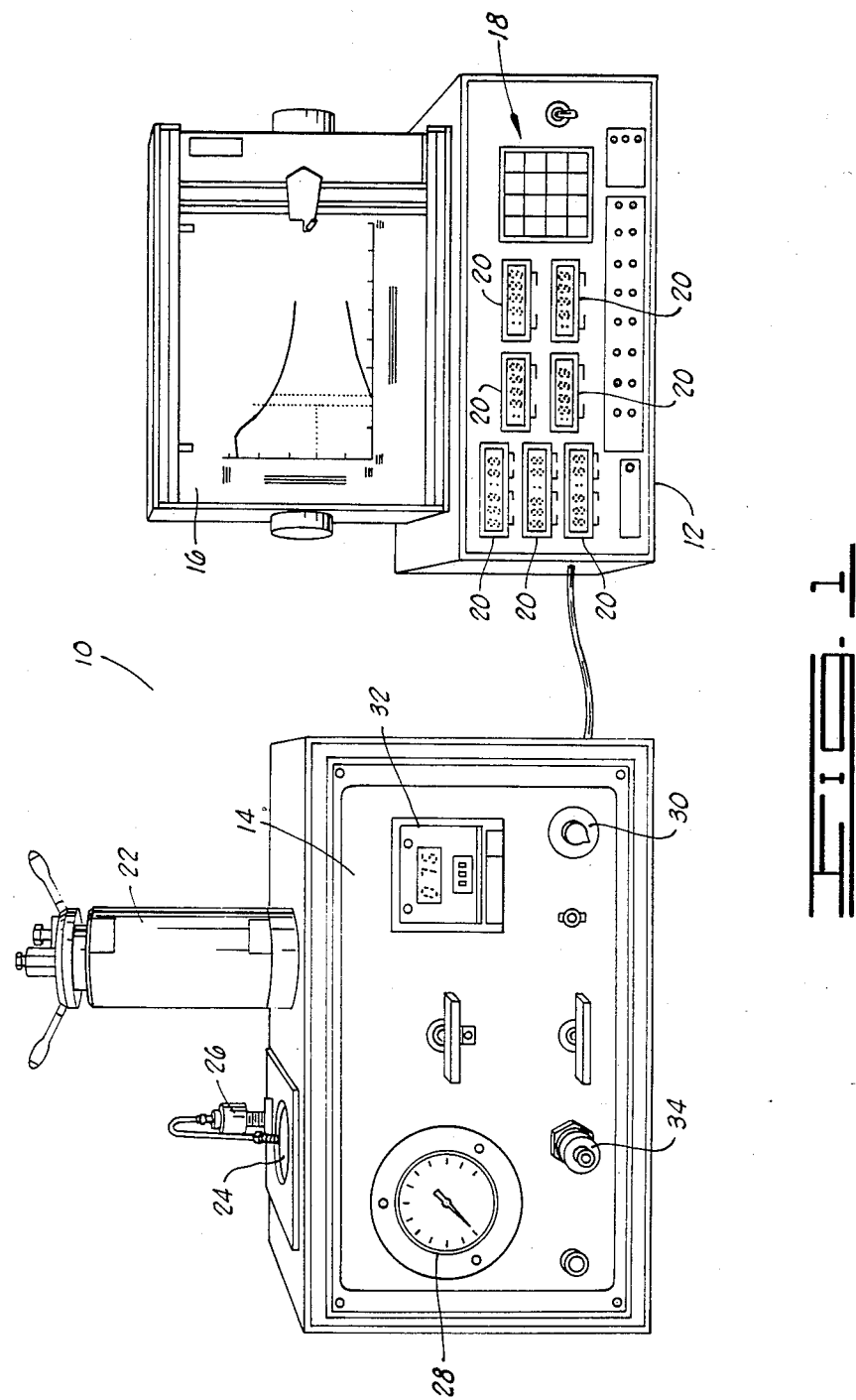
FIG. 1 is a view illustrating a cement analyzing system in which the present invention is embodied.

Referring to FIG. 1, the components of a cement analyzer system 10 are shown.

A control computer 12 having a multichannel capability is shown connected to a single sample measurement autoclave 14. The system 10 may have multiple autoclaves 14 connected in parallel simultaneously. Further connected to the control computer 12 is digital plotter 16. The control computer 12 is provided with keyboard 18 for entering data and command functions and readout displays 20 for displaying various parameters of the system 10.

The autoclave 14 is provided with cement chamber assembly 22 which contains the cement sample being analyzed and the ultrasonic transducers (not shown) which are acoustically coupled thereto during the analysis. The cement sample is placed inside cement sample assembly 22 which is subsequently inserted into an opening 24 in the top of autoclave 14 where it is connected to pressure line 26. A gauge 28 on the autoclave 14 monitors the pressure applied to the sample in the cement chamber assembly 22. The rate of the temperature rise of the sample in the cement chamber assembly 22 is controlled by variable transformer control 30 which controls the current through a heater coil therein (not shown). The temperature measured at the cement chamber assembly is controlled and displayed on temperature control unit 32. The pressure for pressuring up the cement chamber assembly 22 is supplied through an external connection 34 on the front of autoclave 14.

Referring to FIG. 2, the prior art cement chamber assembly 22 is shown.

The prior art cement chamber assembly 22 comprises a body 52, top 54, bottom 56, and seals 58.

The body 52 comprises an annular cylindrical member having, on the exterior thereof, first cylindrical surface 60, second cylindrical surface 62 and third cylindrical surface 64 and, on the interior thereof, first annular chamfered surface 66, first threaded bore 68, first cylindrical bore 70, second annular chamfered surface 72, second cylindrical bore 74, frusto-conical bore 76 having a larger diameter in its top portion 78 than bottom portion 80, third cylindrical bore 82, third annular chamfered surface 84, fourth cylindrical bore 86, second threaded bore 88, and fourth annular chamfered surface 90.

The top 54 comprises a circular member having, on the exterior thereof, first annular frusto-conical surface 92, first cylindrical surface 94, second annular frusto-conical surface 96, second cylindrical surface 98, threaded surface 100 which releasably threadedly engages first threaded bore 68 of body 52, fourth cylindrical surface 102 having, in turn, annular recess 104 therein containing annular elastomeric seal 58 therein which sealingly engages second cylindrical bore 72 of body 52 and fifth cylindrical surface 106. The top 54 further includes blind bore 108 therein, threaded bore 110 concentrically located with respect to first bore 112 and having, in turn, lateral bore 114 intersecting near the bottom thereof and second threaded bore 116 concentrically located with respect to bore 118 and having lateral bore 120 intersecting near the bottom thereof.

The bottom 56 comprises a circular member having, on the exterior thereof, first frusto-conical annular surface 122, first cylindrical surface 124, second frusto-conical annular surface 126, second cylindrical surface 128, threaded surface 130 which threadedly releasably engages second threaded bore 88 of body 52, third cylindrical surface 132 and fourth cylindrical surface 134 upon which annular elastomeric seal 58 is retained to sealingly engage third cylindrical bore 82 of body 52. The bottom 56 further includes first blind bore 136, second blind bore 138, and third blind bore 140.

Referring to FIG. 3, the cement chamber assembly 150 of the present invention is shown.

The cement chamber assembly 150 comprises body 152, top 154, bottom 156 and seal assembly 158.

The body 152 comprises an annular cylindrical member having, on the exterior thereof from top to bottom, first cylindrical surface 160, second cylindrical surface 162, and third cylindrical surface 164 and, on the interior thereof from top to bottom, first annular chamfered surface 166, first threaded bore 168, first cylindrical bore 170, divergent frusto-conical bore 172 which diverges from the top to the bottom of the body 152, second cylindrical bore 174, second threaded bore 176, and second annular chamfered surface 178.

The top 154 comprises a cylindrical member having, on the exterior thereof, first frusto-conical annular surface 180, first cylindrical surface 182, second frusto-conical annular surface 184, second cylindrical surface 186, threaded surface 188 which releasably, threadedly engages first threaded bore 168 of body 152, third cylindrical surface 190, third frusto-conical surface 192, fourth cylindrical surface 194 having, in turn, annular recess 196 therein, and fourth frusto-conical surface 198. The top 154 further includes, in the center thereof, first annular chamfered surface 200, first bore 202, second annular chamfered surface 204 and blind second bore 206 and, in the peripheral portion of the top, threaded apertures 208 which are centered above cylindrical bores 210 which, in turn, extend through the top 154 and intersected by lateral bores 212 which extend to the periphery of the top 154.

The bottom 156 comprises a cylindrical member having, on the exterior thereof, first frusto-conical surface 214, first cylindrical surface 216, second frusto-conical surface 218, second cylindrical surface 220, threaded surface 222 which releasably, threadedly engages second threaded bore 176 in body 152, third cylindrical surface 224, third frusto-conical surface 226, and fourth cylindrical surface 228 having, in turn, annular recess 230 therein. The bottom 156 further includes, in the center thereof, first annular chamfered surface 232, first cylindrical bore 234, second annular chamfered surface 236 and blind second cylindrical bore 238 and, in the periphery thereof, blind cylindrical bores 240.

Referring to FIG. 4, the seal assembly 158 is shown in an enlarged view in relation to the top 154, however, the seal assembly 158 also seals the bottom 156.

The seal assembly 158 comprises annular resilient cylindrical ring 250 which is, in turn, contained in annular recess 196 of top 154 for example, although it could also be retained in annular recess 230 of bottom 156, annular elastomeric seal 252 which is retained on fourth cylindrical surface 194 of top 154 and slidingly sealingly engages first cylindrical bore 170 of body 152 and annular wedge ring 254 which has a first side thereof 256 engaging annular elastomeric seal 252, a second side thereof formed at an angle complementary to third frusto-conical surface 192 of top 154 to slidingly, sealingly engage the same when assembled, a third cylindrical side 258 which slidingly, sealingly engages first cylindrical bore 170 of body 152 and fourth side 260.

The improved cement chamber assembly 150 of the present invention offers significant improvement in the detection of the first arrival of the signal from the transmitter transducer by reducing the distance between the transmitting transducer in bore 206 and the receiving transducer in bore 238 and increasing any other path that the signal from the transmitting transducer might take, other than through the cement sample contained within divergent frusto-conical bore 172, through the top 154, body 152, and the bottom 156 to the receiving transducer in bore 238.

Referring to FIGS. 2 and 3, when compared to the prior art, the cement chamber assembly 150 of the present invention has the distance between the bottom 242 transmitting transducer bore 206 in the top 154 closer to the top 244 of the receiving transducer bore 238 in the bottom 156 than the distance between the bottom 109 of the transmitting transducer bore 108 in top 54 and the top 137 of the receiving transducer bore 136 in bottom 56 of the cement chamber assembly 22, the cement sample portion has a divergent frusto-conical shape 172 rather than a convergent frusto-conical shape 76 as the cement chamber assembly 22, the divergent frusto-conical shape 172 at any cross-section has a larger diameter than that of a corresponding cross-section in the convergent frusto-conical shape 76 in the cement chamber assembly 22, and an improved seal assembly 158 comprising resilient ring 250, annular elastomeric seal 252 and wedge ring 254.

These improvements allow the enhancement of the detection of the arrival of the first wave signal from the transmitting transducer and an improved sealing arrangement so that the cement chamber assembly is capable of operation at higher pressure levels without leakage.

It will be obvious to those skilled in the art that additions, modifications and deletions in the cement chamber assembly 150 of the present invention may be made which fall within the scope of the invention. It is therefore the aim of the appended claims to cover all such additions, modifications and deletions as fall within the true spirit and scope of the invention.

Having thus described our invention, we claim:

1. An improved fluid chamber assembly used in an apparatus for the nondestructive testing of cement or any fluid by the transmission of a signal through said cement or any fluid by a transmitter transducer and the reception thereof by a receiving transducer, said transmitter transducer and said receiving transducer being acoustically coupled in the improved fluid chamber assembly during said testing, the improved fluid chamber assembly having a shape which facilitates the detection of the first arrival of said signal from said transmitter transducer by said receiving transducer, the improved fluid chamber assembly comprising:
a body having a divergent frusto-conical fluid sample portion from the top to bottom thereof;
a top having a transmitting transducer bore therein adapted to receive said transmitter transducer therein;
a bottom having a receiving transducer bore therein adapted to receive said receiving transducer therein;
a first seal assembly sealingly engaging the body and the top; and
a second seal assembly sealingly engaging the body and the bottom
whereby the improved fluid chamber assembly facilitates the detection of the first arrival of said signal from said transmitter transducer by said receiving transducer by reducing the distance between said transmitting transducer in the top and said receiving transducer in the bottom and by increasing any other path that said signal from said transmitting transducer might follow, other than through said cement or any fluid contained within the divergent frusto-conical fluid sample portion of the body, through the top, body and the bottom to said receiving transducer therein.

2. The improved fluid chamber assembly of claim 1 wherein:
the first seal assembly comprises:
a resilient ring;
an elastomeric seal; and
a wedge ring; and
the second seal assembly comprises:
a resilient ring;
an elastomeric seal; and
a wedge ring.

3. The improved fluid chamber assembly of claim 2 wherein:
the top includes an annular recess in a portion of the periphery thereof which receives the resilient ring of the first seal assembly therein; and the bottom includes an annular recess in a portion of the periphery thereof which receives the resilient ring of the second seal assembly therein.

4. The improved fluid chamber assembly of claim 3 wherein:

the elastomeric seal of the first seal assembly is disposed between the resilient ring and wedge ring of the first seal assembly; and the elastomeric seal of the second seal assembly is disposed between the resilient ring and wedge ring of the second seal assembly.

5. The improved fluid chamber assembly of claim 4 wherein:

the wedge ring of the first seal assembly has a portion engaging the elastomeric seal, a portion engaging the body and a portion engaging the top; and the wedge ring of the second seal assembly has a portion engaging the elastomeric seal, a portion engaging the body and a portion engaging the bottom.

6. The improved fluid chamber assembly of claim 5 wherein:

the top includes a frusto-conical surface engaging the wedge ring of the first seal assembly; and the bottom includes a frusto-conical surface engaging the wedge ring of the second seal assembly.

7. The improved fluid chamber assembly of claim 6 wherein:

the body includes a cylindrical bore sealingly engaging the elastomeric seal and the wedge ring of the first seal assembly and another cylindrical bore sealingly engaging the elastomeric seal and the wedge ring of the second seal assembly.

8. The improved fluid chamber assembly of claim 7 wherein:

the body comprises:

an annular cylindrical member having,
  on the exterior thereof;
    a first cylindrical surface, a second cylindrical surface, and a third cylindrical surface; and,
  on the interior thereof;
    a first annular chamfered surface, first threaded bore, first cylindrical bore, divergent frusto-conical bore which diverges from the top to the bottom of the body, second cylindrical bore, second threaded bore and second annular chamfered surface.

9. The improved fluid chamber assembly of claim 8 wherein:

the top comprises:

a cylindrical member having,
  on the exterior thereof;
    a first frusto-conical annular surface, a first cylindrical surface, a second frusto-conical annular surface, second cylindrical surface, a threaded surface which releasably, threadedly engages the first threaded bore of the body, a third cylindrical surface, a third frusto-conical surface, a fourth cylindrical surface having, in turn, an annular recess therein, and a fourth frusto-conical surface; and,
  in the center thereof;
    a first annular chamfered surface, a first bore, a second annular chamfered surface and a blind second bore.

10. The improved fluid chamber assembly of claim 9 wherein:

the bottom comprises:

a cylindrical member having,
  on the exterior thereof;
    a first cylindrical surface, a first frusto-conical surface, a second cylindrical surface, a threaded surface which releasably, threadedly engages the second threaded bore of the body, a third cylindrical surface, a third frusto-conical surface, and a fourth cylindrical surface having, in turn, an annular recess therein; and
  in the center;
    a first annular chamfered surface, a first cylindrical bore, a second annular chamfered surface and a blind cylindrical bore.

* * * * *